(12) United States Patent
Klobusnik

(10) Patent No.: US 9,302,021 B2
(45) Date of Patent: Apr. 5, 2016

(54) METHOD OF PERFORMING STERILIZATION CYCLE

(71) Applicant: American Sterilizer Company, Mentor, OH (US)

(72) Inventor: Kenneth J Klobusnik, Lake City, PA (US)

(73) Assignee: AMERICAN STERILIZER COMPANY, Mentor, OH (US)

(*) Notice: Subject to any disclaimer, the term of this patent is extended or adjusted under 35 U.S.C. 154(b) by 0 days.

(21) Appl. No.: 14/468,654

(22) Filed: Aug. 26, 2014

(65) Prior Publication Data

US 2015/0064067 A1 Mar. 5, 2015

Related U.S. Application Data

(60) Provisional application No. 61/872,256, filed on Aug. 30, 2013.

(51) Int. Cl.
*A61L 2/20* (2006.01)
(52) U.S. Cl.
CPC ............ *A61L 2/208* (2013.01); *A61L 2202/122* (2013.01); *A61L 2202/13* (2013.01); *A61L 2202/24* (2013.01)

(58) Field of Classification Search
CPC .......................................................... A61L 2/20
USPC ............................................................. 422/33
See application file for complete search history.

(56) References Cited

U.S. PATENT DOCUMENTS

| 4,241,010 A | 12/1980 | Baran ................................ 422/2 |
| 4,372,916 A | 2/1983 | Chamberlain et al. ......... 422/111 |
| 4,973,449 A | 11/1990 | Kolstad et al. ................... 422/27 |
| 5,261,250 A | 11/1993 | Missimer ......................... 62/55.5 |
| 5,527,508 A | 6/1996 | Childers et al. ................... 422/33 |
| 6,010,662 A | 1/2000 | Lin et al. ........................... 422/33 |
| 2010/0086438 A1 | 4/2010 | Larsson et al. ................... 422/26 |
| 2012/0275953 A1* | 11/2012 | Lukasik .................. A61L 2/208 422/28 |

OTHER PUBLICATIONS

Meszaros et al., Area fumigation with hydrogen peroxide vapor, 2005, Applied Biosafety, 10(2), p. 91-100.*

* cited by examiner

*Primary Examiner* — Sean E Conley
*Assistant Examiner* — Holly Mull
(74) *Attorney, Agent, or Firm* — Kusner & Jaffe; Michael A. Centanni

(57) ABSTRACT

A method of sterilizing articles, using a low-vapor-pressure sterilant in a compact sterilizer, including a pre-pulse injection of sterilant to condition a sterilization chamber.

4 Claims, 5 Drawing Sheets

METHOD OF PERFORMING STERILIZATION CYCLE

RELATED APPLICATIONS

This application claims the benefit of U.S. Provisional Application No. 61/872,256, filed Aug. 30, 2013, which is fully incorporated herein by reference.

FIELD OF THE INVENTION

The present invention relates generally to sterilization of articles and, more particularly, to a method of sterilizing articles using vapor compression of low-vapor pressure chemical vapor sterilants.

BACKGROUND OF THE INVENTION

U.S. Pat. No. 5,527,508 to Childers et al. discloses a method for enhancing the penetration of vapor sterilants into openings and apertures of complex objects. The patent discloses a method that includes a plurality of sterilant injection phases. During each sterilant injection phase, a predetermined amount of sterilant is injected into a chamber containing articles to be sterilized under vacuum. As a result of the injection of the sterilant, the pressure in the chamber increases to a pressure greater than the initial pressure in the chamber. The sterilant vapor is allowed to distribute itself through the chamber for a period of time. A compression gas is then introduced into the closed chamber in an amount effective to raise the pressure in the chamber to a sub-atmosphere pressure to drive the vapor sterilant into lumens or passageways of the articles to be sterilized.

Conventional sterilization cycles typically employ four of the aforementioned "sterilant injection phases" to effect sterilization of the articles or instruments within the sterilizer.

The method disclosed in the foregoing patent is typically utilized in sterilizers having sterilization chambers dimensioned between 150 cubic feet and 160 cubic feet. (The examples set forth in U.S. Pat. No. 5,527,508 disclose tests conducted in a 154-cubic-foot chamber.)

In recent years, there has been a desire for smaller and smaller sterilizers for sterilizing smaller instruments in shorter periods of time. Small sterilizers, having sterilization chambers of approximately 50 cubic feet, have become desirable for use in medical offices and similar facilities. It was thought that the method disclosed in the aforementioned U.S. patent could be scaled down for application in such smaller sterilizers. However, it was found that, when the disclosed method was scaled down for use in smaller sterilizers, the smaller sterilizers cannot pass standardized efficacy testing. In this respect, all efficacy testing on low-temperature, vacuum sterilizers is done by performing half of the standard sterilization cycle. The sterilizer must be able to obtain a $10^6$ lethality standard when only half of the operating cycle is performed. It was found, however, that scaled-down operating cycles could not demonstrate adequate kill in the abbreviated "half cycle" to meet existing standards.

Experimentation revealed that the first pulse of the cycle produced lower than expected sterilant concentration levels in the chamber. It is believed that the inability of the smaller sterilizers to utilize the scaled-down version of the established operating cycle for larger sterilizers was due to the difference in the surface area of the larger and smaller sterilizers. In other words, it is believed that the surface area to volume ratio of the chamber affects the performance of a conventional operating cycle used for larger sterilizers. In this respect, it is believed that initial injection of sterilant coats the inner surface of the chamber when the sterilant is first introduced into the chamber. This sterilant, in vapor form when introduced into the vacuum in the sterilization chamber, is believed to break down on contact with the surfaces within the chamber. It is possible that a catalytic reaction results with the metal within the chamber. Whatever the reason, merely scaling down existing methods of operating a sterilization cycle is not acceptable for smaller sterilization chambers.

The present invention overcomes this and other problems and provides a modified method of operating a sterilization cycle for use in smaller sterilizers.

SUMMARY OF THE INVENTION

In accordance with a preferred embodiment of the present invention, there is provided a method of sterilizing articles using a low-vapor-pressure sterilant, comprising the steps of:

a. evacuating a closed chamber containing an article to a pressure $P_1$ below atmospheric pressure;

b. injecting a predetermined amount of sterilant into the closed chamber sufficient to establish a desired initial level of sterilant vapor in the closed chamber;

c. evacuating the closed chamber to approximately pressure $P_1$;

d. introducing only a sterilant vapor into the closed chamber in an amount effective to raise the pressure in the chamber to a predetermined second subatmospheric pressure $P_2$;

e. allowing the introduced amount of sterilant vapor to diffuse throughout the closed chamber and into the article for a predetermined period of time which is less than or equal to twice the half-life of the sterilant vapor in the chamber;

f. introducing a compression gas into the closed chamber in an amount effective to raise the pressure in the chamber to a third subatmospheric pressure $P_3$ in a compression time period, wherein the third pressure is substantially greater than the second pressure and wherein the pressure differential between the third pressure and the second pressure is effective to drive the diffused sterilant vapor further into the article than the vapor has diffused such that the sterilant vapor substantially penetrates the article; and g. repeating steps (c) through (f) until sterilization of the article is achieved.

An advantage of the present invention is a method of performing a sterilization cycle for a low-temperature sterilizer.

Another advantage of the present invention is a method as described above for a compact, low-temperature sterilizer.

Another advantage of the present invention is a method as described above that utilizes established operating procedures.

A still further advantage of the present invention is to provide a modified method of enhanced penetration of low-vapor pressure chemical vapor sterilants during sterilization.

A still further advantage of the present invention is a method as described above that utilizes the same sterilant throughout the sterilization cycle.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
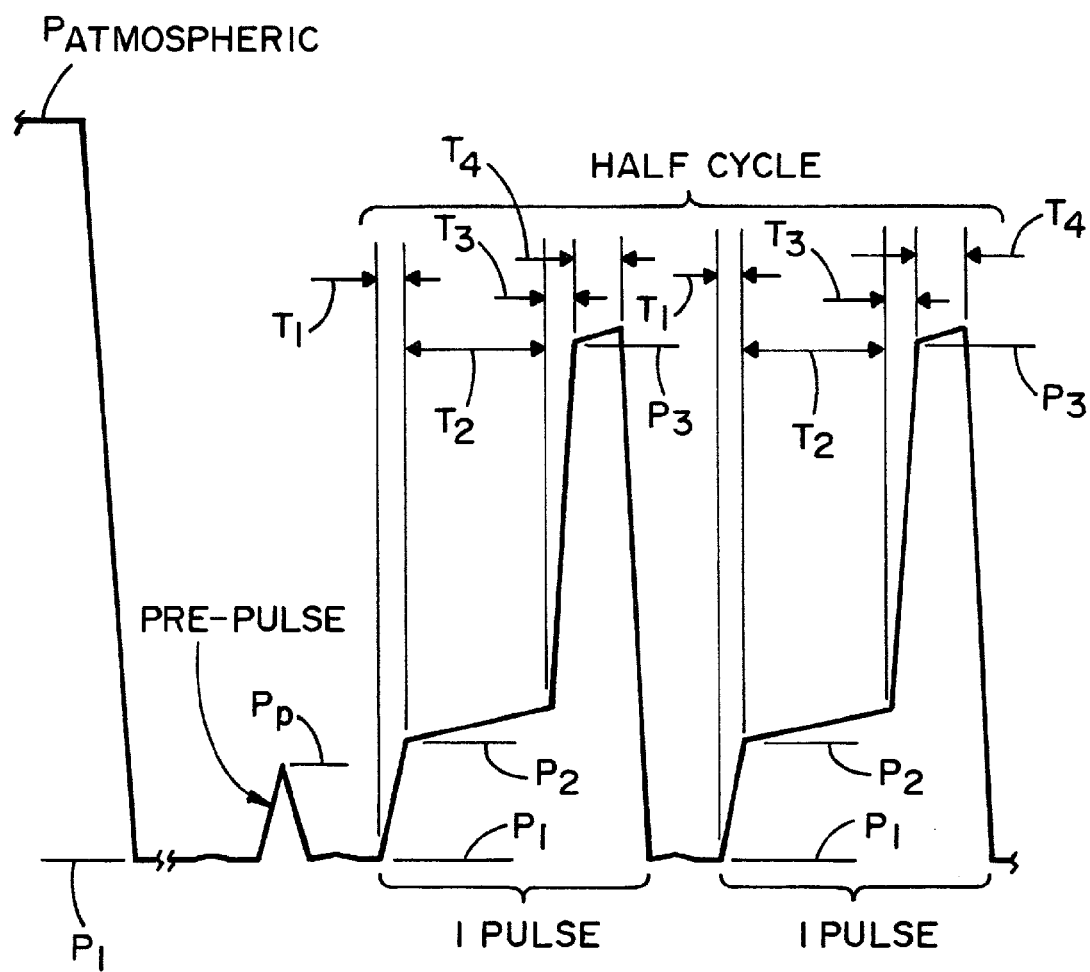
FIG. 1 is a schematic diagram illustrating a portion of a sterilization cycle according to the present invention.

Referring now to the drawing wherein the showing is for the purpose of illustrating a preferred embodiment of the invention only and not for the purpose of limiting same, the invention will be described with reference to FIG. 1, which illustrates a portion of a vapor compression sterilization cycle and shows the pressure within a sterilization chamber over time. Typically, a sterilization chamber is initially at atmospheric pressure (760 Torr). As depicted in FIG. 1, the sterilization chamber is first evacuated to a pre-selected pressure $P_1$, typically less than or equal to 40 Torr.

A predetermined amount of sterilant vapor is then introduced into the chamber, raising the pressure in the chamber to a pre-pulse pressure $P_p$. This introduction of sterilant vapors is identified as a "pre-pulse" in FIG. 1. The amount of sterilant added during this pre-pulse injection is generally based upon the size of the chamber. In this respect, as the size of the sterilization chamber becomes smaller, the surface area-to-volume ratio of the chamber increases.

In accordance with a preferred embodiment of the invention, the amount of hydrogen peroxide injected during the "pre-pulse" is about 10% or more of the amount of hydrogen peroxide injected during a "standard pulse" used during a typical sterilization cycle. In accordance with a more preferred embodiment of the invention, the amount of hydrogen peroxide injected during the "pre-pulse" is between about 10% and about 30% of the amount of hydrogen peroxide injected during a "standard pulse" used during a typical sterilization cycle.

It is believed that initial injections of sterilant will interact with the surfaces within the chamber and break down upon contact with the surfaces. By injecting an initial amount of sterilant within the chamber and allowing it to distribute throughout the chamber, subsequent injections of sterilant into the chamber, as part of a conventional sterilization cycle, will not break down as rapidly and the desired concentration of sterilant in the chamber can be maintained at a desired level to effect sterilization. In this respect, the amount of sterilant injected during this pre-pulse injection is related to the amount of sterilant injected during a normal sterilant injection phase of a sterilization cycle.

Following the pre-pulse injection of sterilant, the sterilization chamber is evacuated to essentially be pre-selected pressure $P_1$. After a short period of time, $T_p$, that allows the sterilant injected during the pre-pulse to dissipate throughout the chamber, a sterilant injection phase, identified as a "pulse" in FIG. 1 is initiated. During the sterilant injection phase (pulse), sterilant vapors are introduced into the chamber, raising the pressure in the chamber to a second predetermined pressure, $P_2$ typically at least twice $P_1$ in a predetermined Time $T_1$. $P_2$ is limited by the nature of the low-pressure sterilant. The vapor is allowed to distribute itself throughout the chamber (including the dead end lumens) for a predetermined time $T_2$, which is normally less than or equal to twice the half life of the sterilant based upon the environment within the chamber.

The vapor compression begins by admitting the air, dry air sterilant laden air or inert gas ("Pressure Gas") into the chamber. The Pressure Gas is admitted into the chamber raising the pressure to a third predetermined pressure, $P_3$, within a third predetermined Time $T_3$. Time $T_3$ is typically less than one minute in duration. Pressure $P_3$ is typically greater than six times pressure $P_2$. The Pressure Gas and sterilant are then allowed to remain inside the tube for a fourth predetermined time, $T_4$, which is normally greater than or equal to the half of the sterilant life while inside the tube. The chamber is then evacuated again to pressure $P_1$ and another sterilant injection phase is repeated.

The pressure, time ranges and number of pulsations will vary between articles, depending on the particular object and its application. The following are but illustrative examples of the present invention as applied on various samples.

As illustrated in FIG. 1, the pressure rise of sterilant injected during the pre-pulse is typically less than the pressure rise of sterilant injected during each sterilant injection phase (pulse).

To show the effects of adding a pre-pulse injection to a sterilization cycle, two test cycles were run. Both test cycles were performed using the same sterilizer having a sterilization chamber with a capacity of about 60 liters. Equal amounts of sterilant were injected during each of the two test cycles, and the test cycles were operated at similar pressures.

Figure 2:
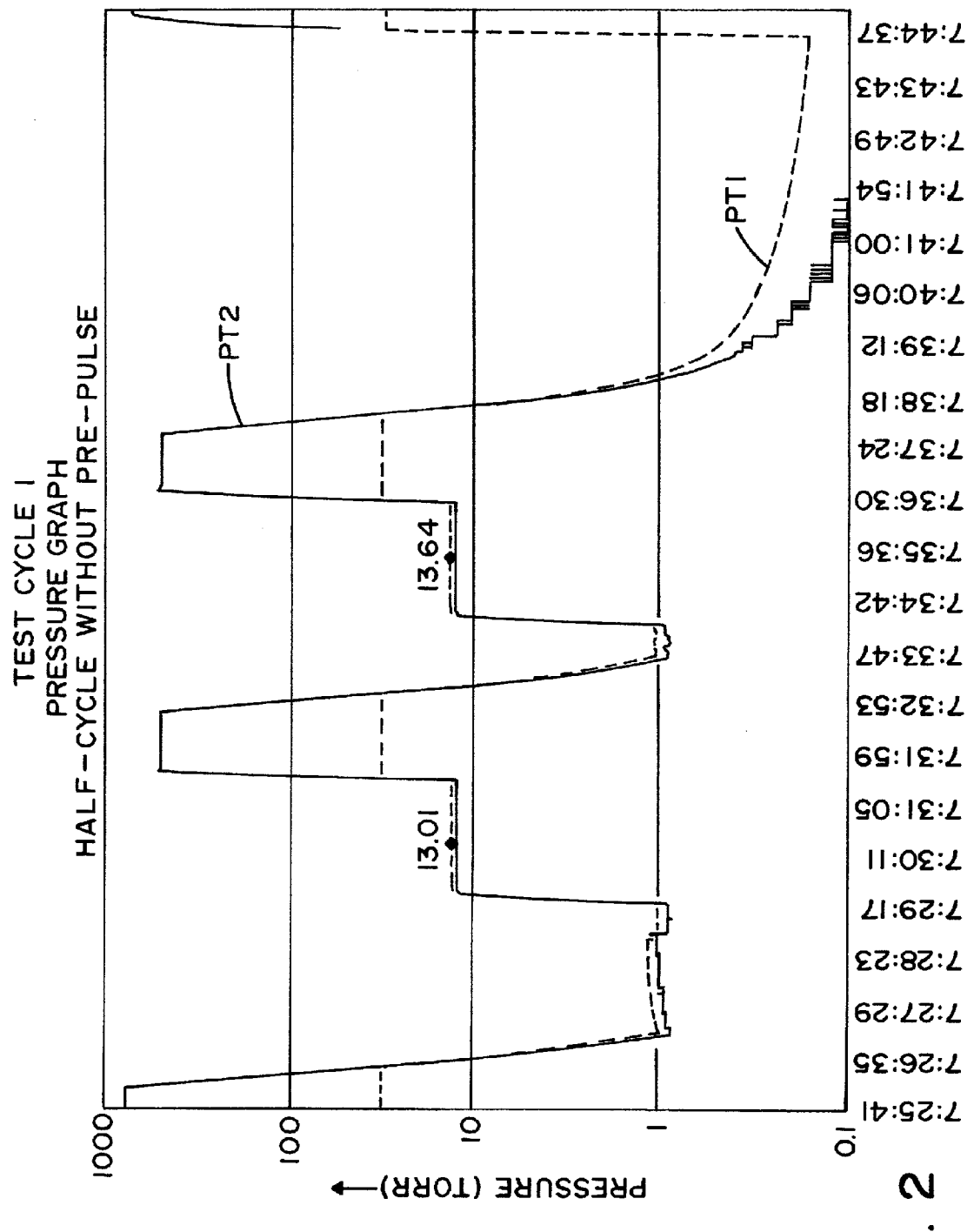
FIG. 2 is a pressure/time graph of a first sterilization half-cycle test without a pre-pulse injection.
Figure 3:
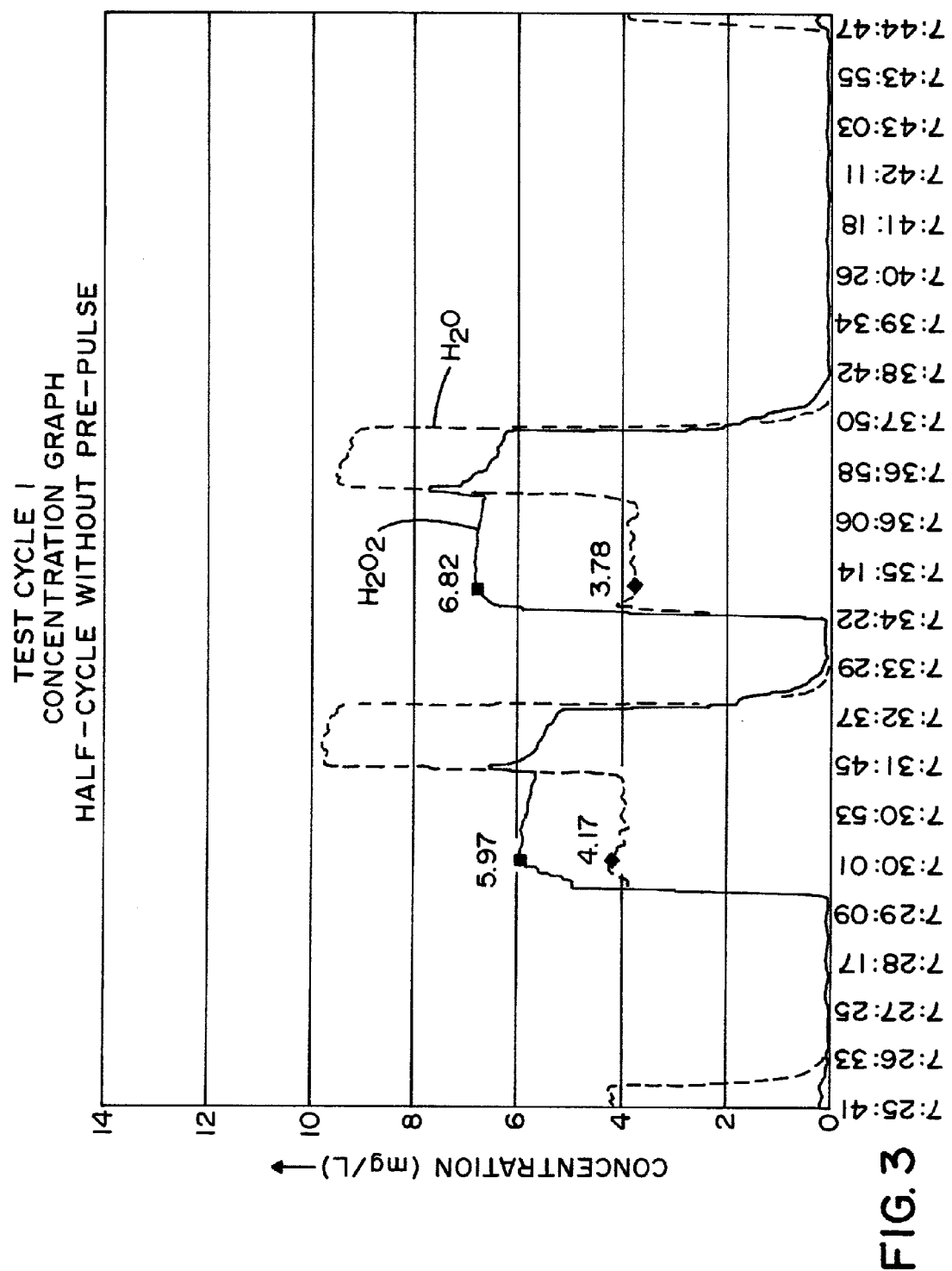
FIG. 3 is a concentration graph corresponding to the first sterilization half-cycle test shown in FIG. 2.

The first test cycle (Test Cycle 1) was performed without a "pre-pulse" according to the present invention. The second test cycle (Test Cycle 2) was performed with a "pre-pulse" injection of sterilant. FIG. 2 shows a pressure graph for the sterilization half-cycle performed during Test Cycle 1 without a "pre-pulse." In FIG. 2, "PT1" refers to a low pressure transducer detecting low pressure, and "PT2" designates a pressure transducer capable of sensing higher pressures. FIG. 3 is the corresponding concentration graph showing the concentration of hydrogen peroxide within the sterilization chamber during each of the pulses during the half-cycle of Test Cycle 1. As shown in FIG. 3, the level of concentration resulting from the first pulse of sterilant was lower than the level of sterilant resulting from the second pulse, despite the fact that both injections injected the same amount of hydrogen peroxide into the sterilizing chamber.

FIG. 3 illustrates the aforementioned phenomenon, wherein a portion of the first sterilant injection appears to break down when injected into the sterilizing chamber. As indicated above, it is believed that surfaces within the chamber, i.e., the inner surface of the sterilizing chamber and the articles within the chamber, break down some of the sterilant upon initial contact.

Figure 4:
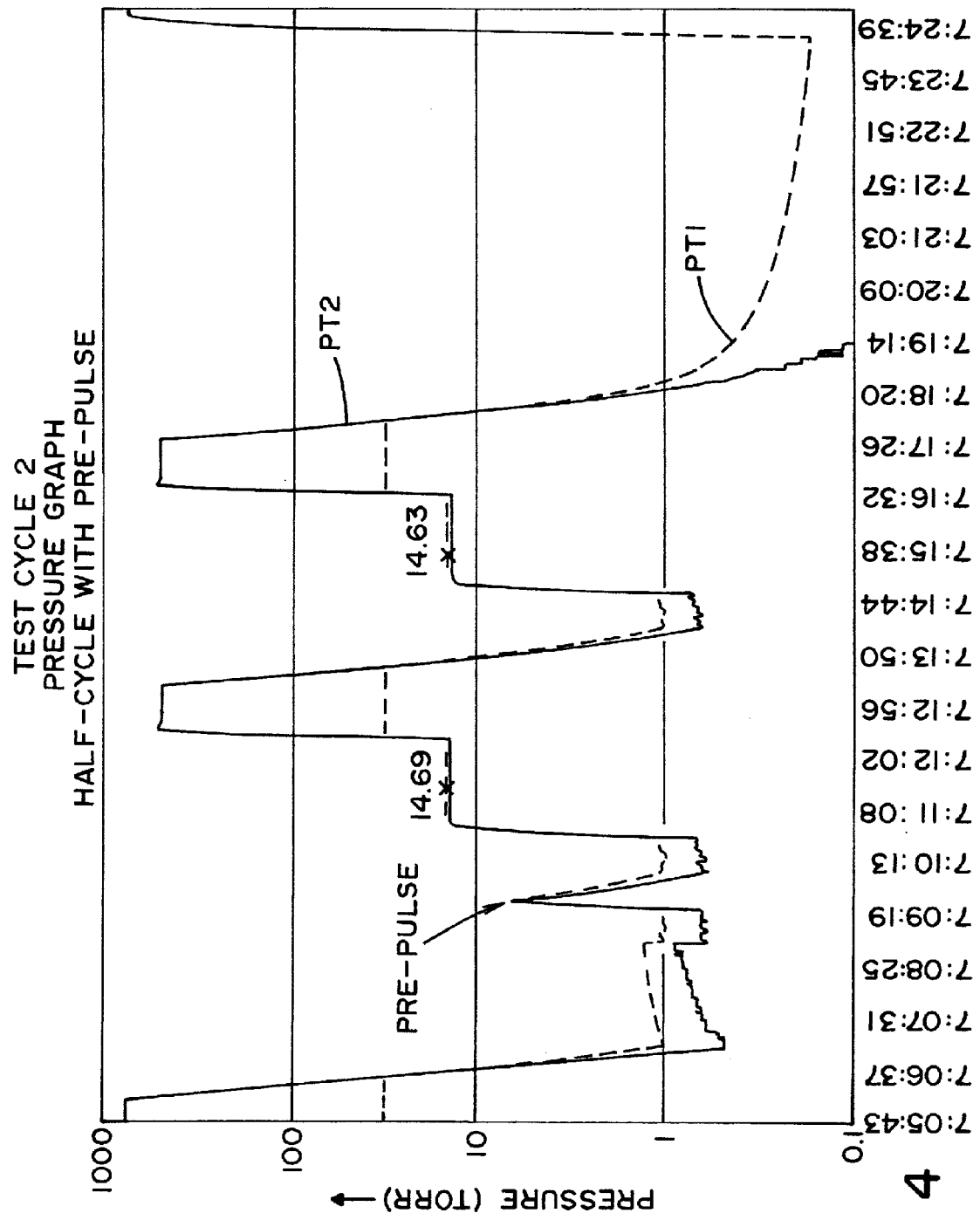
FIG. 4 is a pressure/time graph of a second sterilization half-cycle test with a pre-pulse injection.
Figure 5:
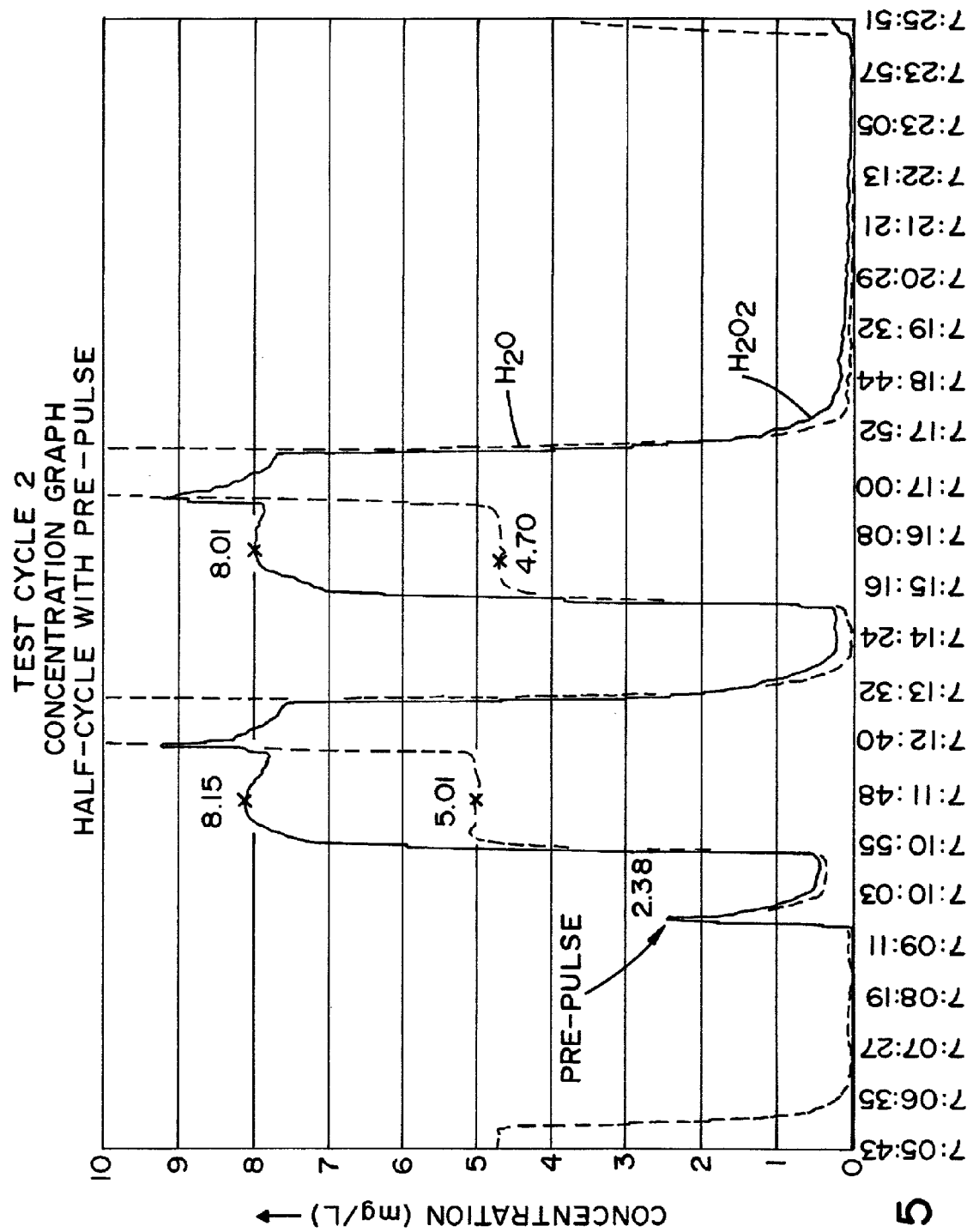
FIG. 5 is a concentration graph corresponding to the second sterilization half-cycle test shown in FIG. 4.

Referring now to FIGS. 4 and 5, a second test cycle (Test Cycle 2) was performed. FIG. 4 shows a pressure graph and illustrates a spike in pressure where a "pre-pulse" of sterilant is injected into the sterilizing chamber. Subsequent pulses, i.e., injections of sterilant, similar to the pulses shown in Test Cycle 1 are also shown. FIG. 5 illustrates the concentration of sterilant within the sterilizing chamber. As shown in FIG. 5, the subsequent pulses of sterilant in the chamber produce similar levels of concentration within the chamber. The pre-pulse thus provides a method of insuring that injection levels calculated for conventional operating cycles are met by injecting a small amount of sterilant into a sterilizing chamber to "prime" the chamber with sterilant so as to avoid break-down of sterilant during subsequent injections (i.e., pulses) in a normal operating cycle. In Test Cycle 2, the amount of sterilant (hydrogen peroxide) injected during the pre-pulse was equal to the amount of sterilant (hydrogen peroxide) injected during the subsequent pulses. Immediately after the initial injection of the sterilant, the chamber is evacuated to remove the hydrogen peroxide that was just introduced into the chamber. This results in the sharp peak of the pre-pulse injection shown in FIG. 4.

As indicated above, during Test Cycle 2, the amount of sterilant (hydrogen peroxide) injected during the pre-pulse was equal to the amount of sterilant injected during a standard pulse. The reason for this is because the injection system used during the test was not capable of metered injections. In other words, the injection system used during Test Cycle 2 could only inject a "full" dose of sterilant during an injection cycle. However, as noted above, it is believed that a pre-pulse injection of 10% or more of a standard pulse is sufficient to prevent the concentration of the first pulse of sterilant from being significantly lower than the concentration of the second pulse.

As described above in the BACKGROUND section of the application, sterilization cycles are typically tested by performing half the normal operating cycle. Since a "half cycle" that includes the addition of the pre-pulse to the first two standard pulses of a four (4)-pulse sterilization cycle is not in fact "half" of a conventional four (4)-pulse cycle, it is contemplated that the full sterilization cycle could be modified to include a second "pre-pulse" (like the first pre-pulse) before the third and fourth standard pulses. In other words, it is contemplated that a full sterilization cycle could be comprised of two half cycles as shown in FIG. 1.

The present invention thus provides a modified sterilization cycle for use with a smaller sterilization chamber, which sterilization cycle can be carried out using an existing injection system from a larger sterilizer.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method of sterilizing articles using a low-vapor-pressure sterilant, comprising the steps of:
   a. evacuating a closed chamber containing an article to a pressure $P_1$ below atmospheric pressure;
   b. injecting a predetermined amount of a sterilant vapor into said closed chamber in a single pre-pulse sufficient to establish a desired initial level of sterilant in said closed chamber;
   c. evacuating said closed chamber to approximately pressure $P_1$;
   d. introducing only sterilant vapor into the closed chamber in an amount effective to raise the pressure in the closed chamber to a predetermined second subatmospheric pressure $P_2$;
   e. allowing the introduced amount of sterilant vapor to diffuse throughout the closed chamber and into the article for a predetermined period of time which is less than or equal to twice the half-life of the sterilant vapor in the closed chamber;
   f. introducing a compression gas into the closed chamber in an amount effective to raise the pressure in the closed chamber to a third subatmospheric pressure $P_3$ in a compression time period, wherein the third pressure is substantially greater than the second pressure and wherein the pressure differential between the third pressure and the second pressure is effective to drive the diffused sterilant vapor further into the article than the vapor has diffused such that the sterilant vapor substantially penetrates the article; and
   g. repeating steps (c) through (f) until sterilization of the article is achieved.

2. A method according to claim 1, wherein said predetermined amount of sterilant vapor injected in said single pre-pulse in step (b) is equal to about 10% or more of the amount of sterilant vapor introduced in step (d).

3. A method according to claim 1, wherein said predetermined amount of sterilant vapor injected in said single pre-pulse in step (b) is equal to about 10% to about 30% of the amount of sterilant vapor introduced in step (d).

4. A method according to claim 1, wherein said predetermined amount of sterilant vapor injected in said single pre-pulse in step (b) is equal to the sterilant vapor introduced in step (d).

* * * * *